United States Patent [19]

Begley et al.

[11] Patent Number: 4,847,185
[45] Date of Patent: Jul. 11, 1989

[54] PHOTOGRAPHIC MATERIAL AND PROCESS (A)

[75] Inventors: William J. Begley; Michael J. Carmody, both of Webster; John M. Buchanan, Rochester, all of N.Y.

[73] Assignee: Eastman Kodak Company, Rochester, N.Y.

[21] Appl. No.: 213,416

[22] Filed: Jun. 30, 1988

[51] Int. Cl.⁴ .................. G03C 7/26; G03C 7/32; G03C 7/36; G03C 7/38
[52] U.S. Cl. .................... 430/376; 430/223; 430/226; 430/512; 430/543; 430/544; 430/551; 430/548; 430/553; 430/555; 430/557; 430/558; 430/559; 430/564; 430/566; 430/607; 430/955; 430/957
[58] Field of Search .............. 430/223, 226, 544, 553, 430/955, 957, 376, 382, 385, 387, 389, 512, 555, 557, 548, 543, 558, 551, 559, 564, 566, 607

[56] References Cited

U.S. PATENT DOCUMENTS 3,311,476  2/1967  Loria .................. 430/555
4,248,962  2/1981  Lau .................... 430/382
4,409,323  10/1983 Sato et al. ............. 430/544

FOREIGN PATENT DOCUMENTS 0255085  2/1988  European Pat. Off. .
60-218645  1/1985  Japan .
61-156126  7/1986  Japan .

Primary Examiner—Richard L. Schilling
Attorney, Agent, or Firm—Richard E. Knapp

[57] ABSTRACT

Photographic compounds capable of releasing a photographically useful group (PUG) by means of an intramolecular nucleophilic displacement provide increased image acutance when a coupling-off group in the coupling position of the compound is a group of the formula:

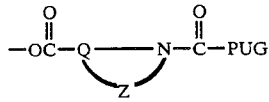

wherein PUG is a photographically useful group; Q is N or C—R where R is hydrogen or a substituent that does not adversely affect imaging; and Z represents atoms completing a non-aromatic, heterocyclic ring. The photographic compounds are useful in photographic materials and processes.

9 Claims, No Drawings

PHOTOGRAPHIC MATERIAL AND PROCESS (A)

This invention relates to new photographic compounds that release photographically useful groups by means of intramolecular nucleophilic displacement during photographic processing and to photographic materials and processes using such compounds.

Various ways are recognized in the photographic art for release of a photographically useful group (PUG) from a compound, such as a coupler, in a photographic material and process. For example, U.S. Pat. No. 4,248,962, describes compounds that release photographically useful groups by means of an intramolecular nucleophilic displacement reaction in photographic materials. These compounds, particularly couplers, capable of releasing a photographically useful group in a photographic material upon processing provide a degree of control over the timing and rate of release as well as the rate of diffusion and distance of diffusion of the photographically useful group in the photographic material.

A need has existed for a compound that not only provides the described release of a photographically useful group, but also provides increased acutance of an image formed in a photographic material containing such compounds during processing. Moreover, such a need has existed with the added parameter that such compounds must not require significantly modifying and photographically useful groups or the carrier compounds, such as the couplers, in a way that would adversely affect the ultimate end use for which each is intended.

The present invention solves these problems by means of a photographic element comprising a support bearing at least one photographic silver halide emulsion layer and at least one compound (A) having in a coupling position a coupling-off group capable of releasing a photographically useful group by means of intramolecular nucleophilic displacement wherein the coupling-off group is represented by the formula:

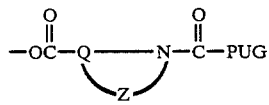

wherein
Q is N or C—$R_1$, where $R_1$ is hydrogen; unsubstituted or substituted alkyl, such as branched or unbranched alkyl containing 1 to 20 carbon atoms, for example, methyl, ethyl, propyl, n-butyl, t-butyl, pentyl, and eicosyl; and unsubstituted or substituted aryl, such as phenyl, chlorophenyl, and naphthyl;
PUG is a photographically useful group; and,
Z represents the atoms necessary to complete a non-aromatic ring, such as a 4-, 5- or 6-member heterocyclic ring.

The described compound (A) is typically represented by the formula:

CAR—LINK—PUG where CAR is a carrier moiety capable of releasing LINK—PUG during photographic processing upon reaction with oxidized developing agent; LINK—PUG is in turn capable of releasing a photographically useful group (PUG) by an intramolecular nucleophilic displacement reaction; and LINK—PUG is represented by the above coupling-off group formula. A preferred compound (A) is a dye-forming coupler.

A process of forming an image having increased acutance comprises developing an exposed photographic element by means of a color developing agent in the presence of described compound (A), particularly a coupler as described.

The compound (A) is, for example, a new coupler represented by the formula:

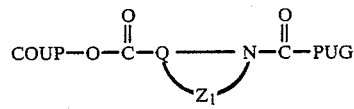

wherein
Q is N or C—$R_1$;
$R_1$ is hydrogen or unsubstituted or substituted alkyl, such as unbranched or branched alkyl containing 1 to 20 carbon atoms, for example methyl, ethyl, propyl, n-butyl, t-butyl and eicosyl;
PUG is a photographically useful group;
$Z_1$ represents the atoms necessary to complete a non-aromatic ring, particularly a 4-, 5- or 6-member heterocyclic ring; and,
COUP is a coupler moiety having the remainder of the molecule attached at the coupling position of the coupler moiety.

The compound A, preferably a development inhibitor releasing (DIR) coupler, contains a coupling-off group—LINK—PUG where PUG is a development inhibitor that enables increased acutance of an image formed upon processing a photographic silver halide element containing the compound (A).

The reaction of compound (A), preferably a coupler, with oxidized color developing agent cleaves the bond between the coupling-off group and the carrier portion of the compound (A), preferably the coupler moiety (COUP). Then the bond between the photographically useful group and the remainder of the coupling-off group is cleaved. Bond cleavage between the PUG and the remainder of the coupling-off group preferably does not involve the action of oxidized color developing agent. The cleavage of the bond between the PUG and the remainder of the coupling-off group is enabled by an intramolecular nucleophilic displacement reaction. Tailoring the structure of the LINK moiety to the requirments of a given PUG enables control over timing and rate of release of the PUG. The sequential cleavage of the bond between the coupling-off group and the carrier portion of the compound (A) and the bond between the PUG and the remainder of the coupling-off group is a characteristic feature of the compounds as described.

It is surprising that merely placing a heterocyclic group containing Z as described between the carboxy portion of the coupling-off group and the carbonyl group adjacent to a development inhibitor PUB enables the increased acutance of an image in a photographic element as described. This is demonstrated by the comparative data in the following examples compared to a known coupler from U.S. Pat. No. 4,248,962 wherein PUG is a development inhibitor moiety.

Particularly useful compounds as described are couplers represented by the formula:

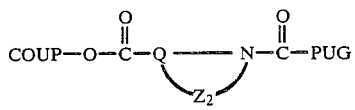

wherein

Q is N or C—R₁;

R₁ is hydrogen, unsubstituted or substituted alkyl, such as methyl, ethyl, propyl, n-butyl, t-butyl or eicosyl, or unsubstituted or substituted aryl, such as phenyl or naphthyl;

Z₂ is (CH₂)$_n$ where n is 3 or 4, or Z₂ completes an indomine or tetrahydroquiniline ring system; and, PUG is a photographically useful group, preferably a releasable development inhibitor group.

Examples of useful LINK-PUG groups in compounds of the invention are as follows:

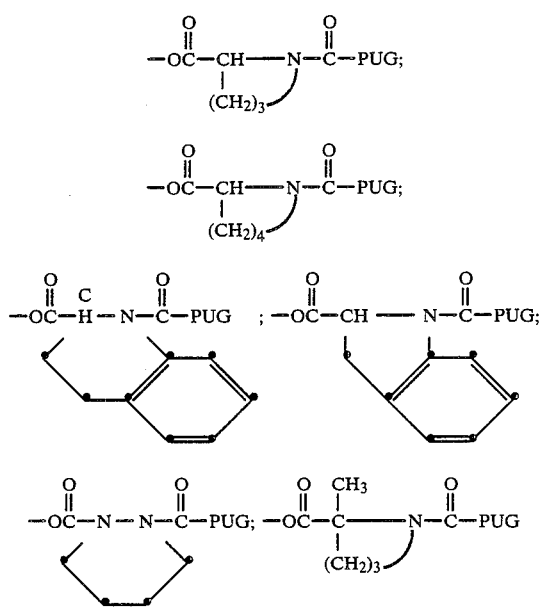

wherein PUG is as described, preferably a releasable development inhibitor moiety.

As used herein the terms "coupler" and "coupler compound" refer to the entire compound, including the coupler moiety, the coupling-off group and the PUG. The term "coupler moiety" refers to that portion of the compound other than the coupling-off group.

The coupler moiety (COUP) can be any moiety that will react with oxidized color developing agent to cleave the bond between the carboxy portion of the coupling-off group and the coupler moiety. The coupler moiety herein includes coupler moieties employed in conventional color-forming couplers that yield colorless products on reaction with oxidized color developing agents as well as coupler moieties that yield colored products on reaction with oxidized color developing agents. Both types of coupler moieties are well known to those skilled in the photographic art.

The coupler moiety can be ballasted or unballasted. It can be monomeric, or it can be part of a dimeric, oligomeric or polymeric coupler, in which case more than one group containing PUG can be contained in the coupler, or it can form part of a bis compound in which the PUG forms part of a link between two coupler moieties.

It will be appreciated that, depending upon the particular coupler moiety, the particular color developing agent and the type of processing, the reaction product of the coupler moiety and the oxidized color developing agent can be: (1) colored and nondiffusible, in which case it will remain in the location in which it is formed, (2) colored and diffusible, in which case it may be removed during processing from the location where it is formed or allowed to migrate to a different location, or (3) colorless and diffusible or non-diffusible in which case it will not contribute to image density.

The coupling-off group is joined to the coupler moiety at the coupling position of the coupler moiety. The coupling-off group is released from the coupling position by oxidative coupling reactions known in the photographic art.

As used herein, the term "intramolecular nucleophilic displacement reaction" means a reaction in which a nucleophilic center of a compound reacts directly, or indirectly through an intervening molecule, at another site of the compound, that is an electrophilic center, to effect displacment of a group or atom attached to the electrophilic center. Such compounds have a nucleophilic group and electrophilic group spacially related by the configuration of the molecule to promote reactive proximity. The electrophilic group and the nucleophilic group are located in the coupling-off group as described so that a cyclic organic ring, or a transient cyclic organic ring can be easily formed by an intramolecular reaction involving the nucleophilic center and the electrophilic center.

A nucleophilic group is understood to be a grouping of atoms one of which is electron rich. This atom is referred to as the nucleophilic center. An electrophilic group is understood to be a grouping of atoms one of which is electron deficient. This is referred to as the electrophilic center.

The PUG can be any group that is typically made available in a photographic element in an imagewise fashion. The PUG can be a photographic reagent or a photographic dye. A photographic reagent herein is a moiety that upon release further reacts with components in the photographic element, such as a development inhibitor, a development accelerator, a bleach inhibitor, a bleach accelerator, a coupler (for example, a competing coupler, a dye-forming coupler, or a development inhibitor releasing coupler (DIR coupler), a dye precursor, a dye, a developing agent (for example, a competing developing agent, a dye-forming developing agent, or a silver halide developing agent), a silver complexing agent, a fixing agent, an image toner, a stablizer, a hardener, a tanning agent, a fogging agent, an ultraviolet radiation absorber, an antifoggant, a nucleator, a chemical or spectral sensitizer or a densensitizer.

The PUG can be present in the coupling-off group as a preformed species or it can be present in a blocked form or as a precursor. The PUG can be for example a preformed development inhibitor or the development inhibiting function can be blocked by being the point of attachment to the carbonyl group bonded to PUG in the coupling-off group. Other examples are a preformed dye, a dye that is blocked to shift its absorption, and a leuco dye.

Preferred compound (A) is a photographic coupler containing a coupler moiety and a PUG containing a hetero atom from Group VA or VIA of the Periodic Table having a negative valence of 2 or 3 bonded to the carbonyl group of the coupling-off group.

There follows a listing of patents and publications which describe representative COUP groups useful in the invention. Also listed are structures of preferred COUP and PUG groups. In these structures Y represents, in the case of a dye forming coupler that is useful with couplers according to the invention, a hydrogen atom or a coupling-off group as described. In the case of couplers according to the invention, Y represents

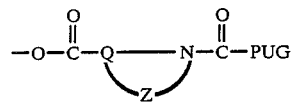

as defined above.

I. COUP's

A. Couplers which form cyan dyes upon reaction with oxidized color developing agents are described in such representative patents and publications as: U.S. Pat. Nos. 2,772,162, 2,895,826, 3,002,836, 3,034,892, 2,474,293, 2,423,730, 2,367,531, 3,041,236, 4,333,999 and "Farbkupplereine Literaturubersicht," published in Agfa Mitteilungen, Band III, pp. 156–175 (1961).

Preferably such couplers are phenols and naphthols which form cyan dyes on reaction with oxidized color developing agent. Structures of preferred such couplers are:

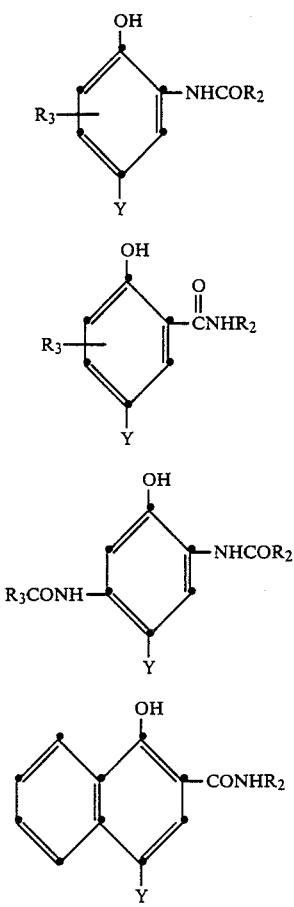

where $R_2$ represents a ballast group, and $R_3$ represents one or more halogen such as chloro or fluoro; alkyl such as methyl, ethyl, butyl; or, alkoxy, such as methoxy, ethoxy, butoxy groups.

B. Couplers which form magenta dyes upon reaction with oxidized color developing agent are described in such representative patents and publications as: U.S. Pat. No. 2,600,788, 2,369,489, 2,343,703, 2,311,082, 3,152,896, 3,519,429, 3,062,653, 2,908,573 and "Farbkupplereine Literaturubersicht," published in Agfa Mitteilungen, Band III, pp. 126–156 (1961).

Preferably, such couplers are pyrazolones and pyrazolotriazoles which form magenta dyes upon reaction with oxidized color developing agents and have the Y attached to the coupling position. Structures of preferred such coupler moieties are:

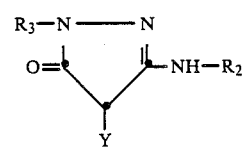

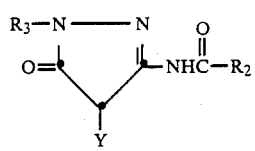

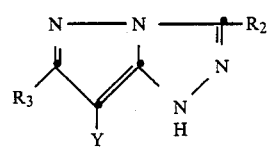

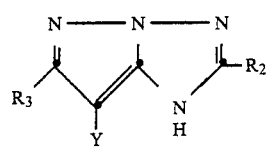

where $R_2$ and $R_3$ are chosen independently to be a ballast group, unsubstituted or substituted alkyl, phenyl or substituted phenyl.

C. Couplers which form yellow dyes upon reaction with oxidized and color developing agents are described in such representative patents and publications as: U.S. Pat. Nos. 2,875,057, 2,407,210, 3,265,506, 2,298,443, 3,048,194, 3,447,928 and "Farbkupplereine Literaturubersicht," published in Agfa Mitteilungen, Band III, pp. 112–126 (1961).

Preferably such yellow-dye forming couplers are acylacetamides, such as benzoylacetanilides and pivaloylacetanilides, and have the Y group attached to the coupling position, that is the active methylene carbon atom.

Structures of preferred such coupler moieties are:

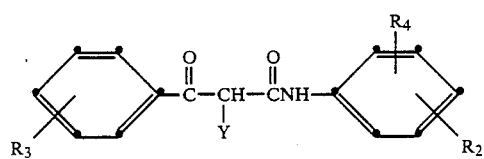

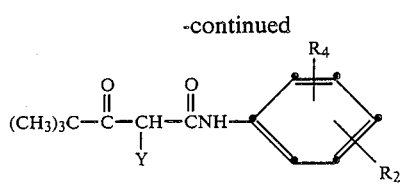

IC-2 where R₂ is as defined above and $R_3$ and $R_4$ are hydrogen or one or more halogen, lower alkyl, such as methyl and ethyl, lower alkoxy, such as methoxy and butoxy, or ballast groups, such as alkoxy of 16 to 20 carbon atoms.

D. Couplers which form colorless products upon reaction with oxidized color developing agent are described in such representative patents as: U.K. Pat. No. 861,138; U.S. Pat. Nos. 3,632,345, 3,928,041, 3,958,993 and 3,961,959. Preferably such couplers are cyclic carbonyl containing compounds which form colorless products on reaction with oxidized color developing agent and have the Y group attached to the carbon atom in the α-position with respect to the carbonyl group.

Structures of preferred such coupler moieties are:

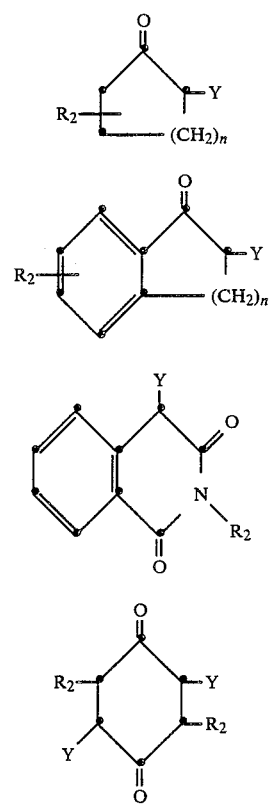

ID-1

ID-2

ID-3

ID-4 where $R_2$ is as defined above and n is 1 or 2.

E. Couplers which form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764.

Preferably such couplers are resorcinols or m-aminophenols which form black or neutral products on reaction with oxidized color developing agent and have the Y group para to a hydroxy group.

Structures of preferred such coupler moieties are:

IE-1

IE-2

IE-3 where $R_5$ is alkyl or 3 to 20 carbon atoms, phenyl or phenyl substituted with hydroxy, halo, amino, alkyl of 1 to 20 carbon atoms or alkoxy of 1 to 20 carbon atoms; each $R_6$ is independently hydrogen, alkyl of 1 to 20 carbon atoms, alkenyl of 1 to 20 carbon atoms, or aryl of 6 to 20 carbon atoms; and $R_g$ is one or more halogen, alkyl of 1 to 20 carbon atoms, alkoxy of 1 to 20 carbon atoms or other monovalent organic groups.

PUG's

A. PUG's which form development inhibitors upon release are described in such representative patents as U.S. Pat. Nos. 3,227,554; 3,384,657; 3,615,506; 3,617,291, 3,733,201 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoazoles, selenobenzoxazoles, mercaptobenzimidazoles, selenobenzimidazoles, oxadiazoles, benzotriazoles and benzodiazoles. Structures of preferred development inhibitor moieties are:

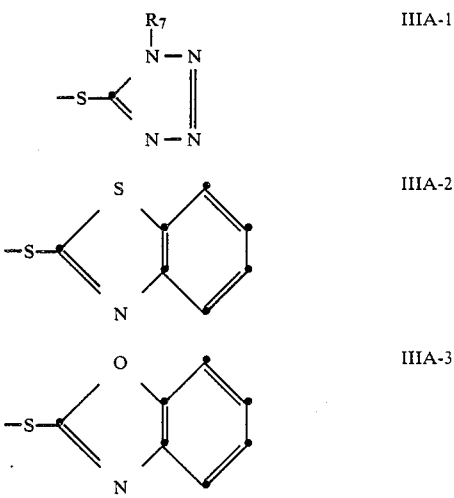

IIIA-1

IIIA-2

IIIA-3

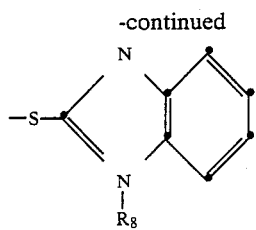

IIIA-4

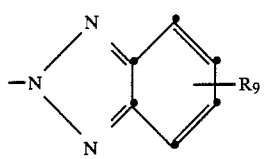

IIIA-5

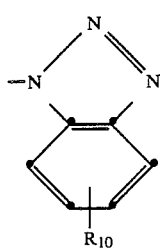

IIIA-6

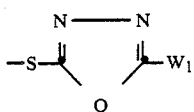

IIIA-7 where $W_1$ is unsubstituted or substituted alkyl, such as butyl, 1-ethylpentyl, and 2-ethoxyethyl, or alkylthio, such as butylthio and octylthio; $R_7$ and $R_8$ are individually hydrogen, alkyl of 1 to 8 carbon atoms such as methyl, ethyl, or butyl, phenyl or substituted phenyl; and $R_9$ and $R_{10}$ are individually hydrogen or one or more halogen such as chloro, fluoro or bromo; alkyl of 1 to 4 carbon atoms, carboxyl, carboxy esters, such as —COOCH$_3$, —NHCOOCH$_3$, —SO$_2$OCH$_3$, —OCH$_2$CH$_2$SO$_2$CH$_3$,

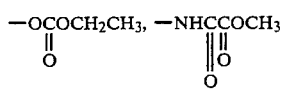

or nitro groups.

B. PUG's which are, or form, dyes upon release:

Suitable dyes and dye precursors include azo, azomethine, azopyrazolone, indoaniline, indophenol, anthraquinone, triarylmethane, alizarin, nitro, quinoline, indigoid and phthalocyanine dyes or precursors of such dyes such as leuco dyes, tetrazolium salts or shifted dyes. These dyes can be metal complexed or metal complexable. Representative patents describing such dyes are U.S. Pat. Nos. 3,880,658; 3,931,144; 3,932,380; 3,932,381; and 3,942,987. Preferred dyes and dye precursors are azo, azomethine and indoaniline dyes and dye precursors. Structures of some preferred dyes and dye precursors are:

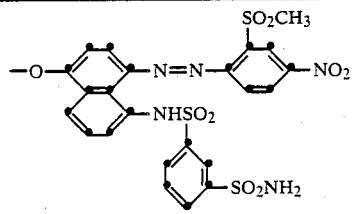

IIIB-1

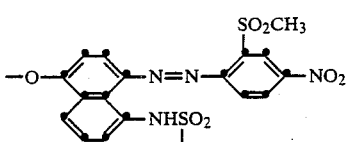

IIIB-2

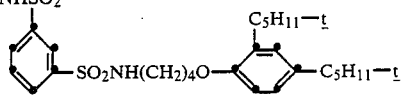

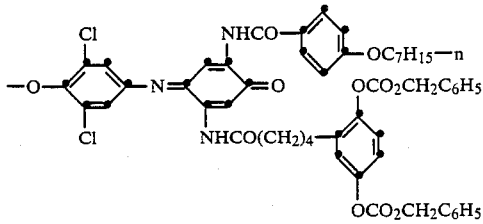

IIIB-3

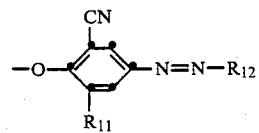

IIIB-4

| $R_{11}$ | $R_{12}$ |
|---|---|
| —H | ![phenyl-SO2N(CH2)2NSO2C16H33 with CH3,CH3] |
| —Cl | ![phenyl-SO2NH-phenyl-OC14H29-n] |
| —Cl | ![phenyl-SO2NH-phenyl with SO2NHC6H13-n, SO2NHC6H13-n] |

C. PUG's which are couplers:

Couplers released can be nondiffusible color-forming couplers, non-color forming couplers or diffusible competing couplers. Representative patents and publications describing competing couplers are: "On the Chemistry of White Couplers," by W. Püschel, Agfa-Gevaert AG Mitteilungen and der Forschungs-Laboratorium der Agfa-Gevaert AG, Springer Verlag, 1954, pp. 352–367; U.S. Pat. Nos. 2,998,314, 2,808,329, 2,689,793; 2,742,832; German Pat. No. 1,168,769 and British Pat. No. 907,274. Structures of preferred competing couplers are:

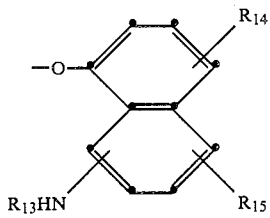
IIIC-1 where $R_{13}$ is hydrogen or alkylcarbonyl, such as acetyl, and $R_{14}$ and $R_{15}$ are individually hydrogen or a solubilizing group, such as sulfo, aminosulfonyl, and carboxy

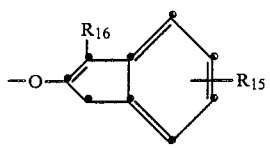
IIIC-2 where $R_{15}$ is as defined above and $R_{16}$ is halogen, aryloxy, arylthio, or a development inhibitor, such as a mercaptotetrazole, such as phenylmercaptotetrazole or ethyl mercaptotetrazole.

D. PUG's which form developing agents:

Developing agents released can be color developing agents, black-and-white developing agents or cross-oxidizing developing agents. They include aminophenols, phenylene diamines, hydroquinones and pyrazolidones. Representative patents are: U.S. Pat. Nos. 2,193,015; 2,108,243; 2,592,364; 3,656,950; 3,658,525; 2,751,297; 2,289,367; 2,772,282; 2,743,279; 2,753;256; and 2,304,953.

Structures of preferred developing agents are:

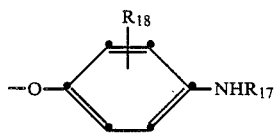
IIID-1 where $R_{17}$ is hydrogen or alkyl of 1 to 4 carbon atoms and $R_{18}$ is hydrogen or one or more halogen such as chloro or bromo; or alkyl of 1 to 4 carbon atoms such as methyl, ethyl or butyl groups.

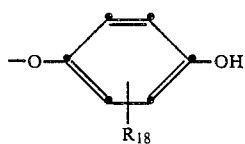
IIID-2 where $R_{18}$ is as defined above.

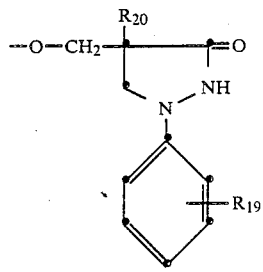
IIID-3

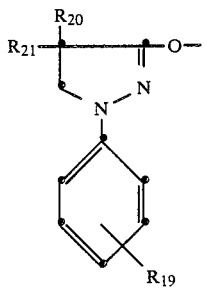
IIID-4

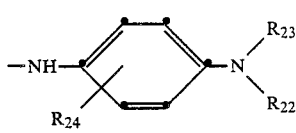
IIID-5

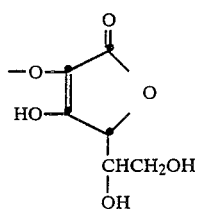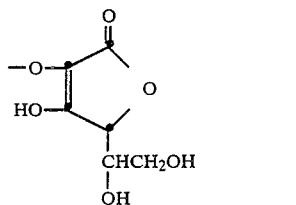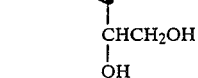
IIID-6 where $R_{19}$ is hydrogen or alkyl of 1 to 4 carbon atoms and $R_{20}$, $R_{21}$, $R_{22}$, $R_{23}$ and $R_{24}$ are individually hydrogen, alkyl or 1 to 4 carbon atoms such as methyl or ethyl; hydroxyalkyl of 1 to 4 carbon atoms such as hydroxymethyl or hydroxyethyl or sulfoalkyl containing 1 to 4 carbon atoms.

E. PUG's which are bleach inhibitors:

Representative patents are U.S. Pat. Nos. 3,705,801; 3,715,208; and German OLS No. 2,405,279. Structures of preferred bleach inhibitors are:

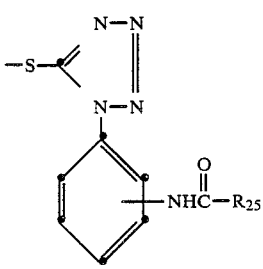
IIIE-1

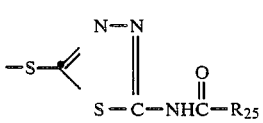
IIIE-2

-continued

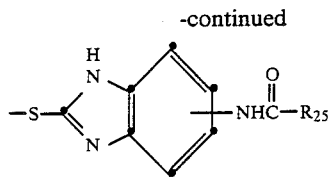
IIIE-3

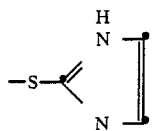
IIIE-4 where $R_{25}$ is an alkyl group of 6 to 20 carbon atoms.

F. PUG's which are bleach accelerators:

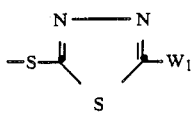
IIIF-1

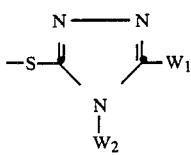
IIIF-2

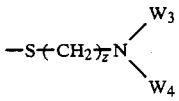
IIIF-3

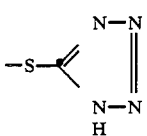
IIIF-4

—SCH$_2$CH$_2$COOH    IIIF-5 wherein $W_1$ is hydrogen, alkyl, such as ethyl and butyl, alkoxy, such as ethoxy and butoxy, or alkylthio, such as ethylthio and butylthio, for example containing 1 to 6 carbon atoms, and which may be unsubstituted or substituted; $W_2$ is hydrogen, alkyl or aryl, such as phenyl; $W_3$ and $W_4$ are individually alkyl, such as alkyl containing 1 to 6 carbon atoms, for example ethyl and butyl; z is 1 to 6.

The Y and particularly the PUG are selected and prepared to adjust to the activity of the adjoining carrier moiety, particularly a coupler moiety and the other groups of the coupler in order to optimize release of the PUG for its intended purpose. Accordingly, PUG groups of differing structural types are useful which enable timing groups having a range of activities. Various properties, such as pKa, are also usefully considered in optimizing the selection of optimum groups for a particular purpose. An example of such a selection could involve, for instance, a benzotriazole moiety as a PUG. Such as benzotriazole moiety can be released too quickly from a timing group which involves an intramolecular nucleophilic displacement mechanism; however, the benzotriazole moiety can be modified from

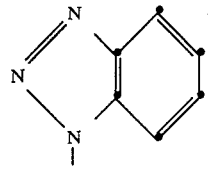

to

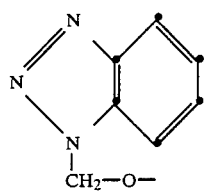

in order to modify the rate at which the benzotriazole moiety is cleaved from the Y. Another illustration of modifying the PUG involves changing, for example, a mercaptotetrazole moiety from

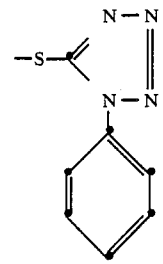

to

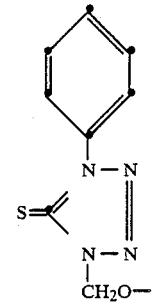

at elevated pH, such as above about pH 10, wherein the —CH$_2$O— portion of the group hydrolyzes rapidly leaving the remainder of the PUG free for its intended purpose.

The compound (A), particularly a photographic coupler, as described, can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration and they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of the invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers as described can be incorporated in or associated with one or more layers or units of the photographic element. For example, a layer or unit affected by PUG can be controlled by incorporating in appropriate locations in the element a scavenger layer which will confine the action of PUG to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure,* January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The photographic couplers can be used in photographic elements in the same way as photographic couplers which release PUGs have previously been used in photographic elements. However, because of the improved ability to control the release of the PUG, the couplers permit enhanced effects or more selective effects. In addition, the couplers can be employed in applications where conventional couplers have previously been employed and a separate component was employed to provide a PUG.

Depending upon the nature of the particular PUG, the couplers can be incorporated in a photographic element for different purposes and in different locations.

When the PUB released from the coupler is a development inhibitor, the coupler can be employed in a photographic element like couplers which release development inhibitors have been used in the photographic art. Couplers of this invention which release a development inhibitor can be contained in, or in reactive association with, one or more of the silver halide emulsion units in a color photographic element. If the silver halide emulsion unit is composed of more than one layer, one or more of such layers can contain the coupler of this invention. The layers can contain other photographic couplers conventionally used in the art. The coupling reaction using couplers of this invention can form dyes of the same color as the color forming coupler(s) in the layer or unit, it can form a dye of a different color, or it can result in a colorless or neutral reaction product. The range of operation between layers of the development inhibitor released from the coupler of this invention can be controlled by the use of scavenger layers, such as a layer of fine grain silver halide emulsion. Scavenger layers can be in various locations in an element containing couplers of this invention. They can be located between layers, between the layers and the support, or over all of the layers.

Photographic couplers as described which release bleach inhibitors or bleach accelerators can be employed in the ways described in the photographic art to inhibit the bleaching of silver or accelerated bleaching in areas of a photographic element.

Photographic couplers as described which release a dye or dye precursor can be used in processes where the dye is allowed to diffuse to an integral or separate receiving layer to form a desired image. Alternatively, the dye can be retained in the location where it is released to augment the density of the dye formed from the coupler from which it is released or to modify or correct the hue of that dye or another dye. In another embodiment, the dye can be completely removed from the element and the dye which was not released from the coupler can be retained in the element as a color correcting mask.

Couplers as described can be employed to release another coupler and the PUG. If the released coupler is a dye-forming coupler it can react with oxidized developing agent in the same or an adjacent layer to form a dye of the same or a different color or hue as that obtained from the primary coupler. If the released coupler is a competing coupler it can react with oxidized color developing agent in the same or an adjacent layer to reduce dye density.

thetic route is shown in following Scheme B. The following description illustrates synthesis Scheme A:

Scheme A

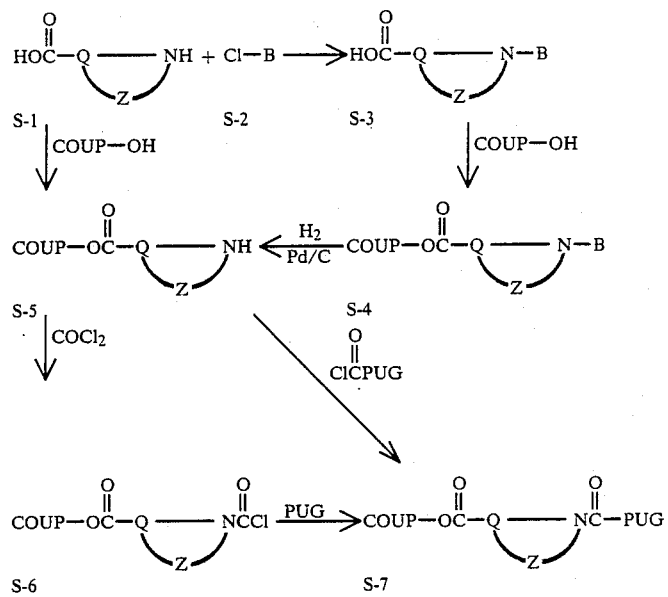

Photographic couplers as described in which the PUG is a developing agent can be used to release a developing agent which will compete with the color forming developing agent, and thus reduce dye density. Alternatively, the couplers can provide, in an imagewise manner, a developing agent which because of such consideration as activity would not desirably be introduced into the element in a uniform fashion.

In chemical systems requiring timed release of a moiety as described herein, the release mechanism can be initiated by any means that initiates cleavage of the coupling-off group from the carrier moiety. Depending on the particular carrier compound, the desired end use of the active moiety, the release mechanism can, for example, be initiated by reaction of the carrier compound with radiation, enzymes, moisture, acid or base, and/or oxidized reducing agent.

Compounds as described can be prepared by reactions and methods known in the organic compound synthesis art. Typically, the couplers as described are prepared as in Scheme A by first attaching the coupling-off group to the coupling position of the coupler moiety without the PUG being present. Then the product is reacted with an appropriate derivative of the PUG to form the desired coupler. An alternative syn- A nitrogen-blocking group B is first attached to amino acid S-1 by treatment with S-2 and the resulting S-3 is allowed to react with the hydroxyl-coupler compound to produce S-4. The blocking group B (typically COOCH$_2$Ph or CH$_2$Ph) is then removed by hydrogenolysis to give the COUP-LINK moiety S-5. S-5 can also be made directly from S-1 by reaction with the hydroxyl-coupler compound, but yields and purity may suffer. Treatment of S-5 with phosgene converts it to the corresponding carbonyl chloride, which can further react with a given PUG to provide the desired COUP—LINK—PUG compound S-7. Alternatively, reaction of a PUG carbonyl chloride with S-5 can give S-7 directly.

Scheme B

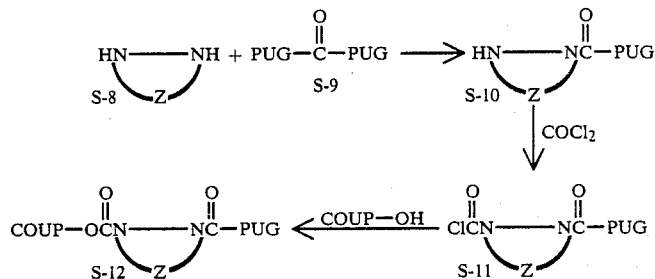

A given PUG group can be attached to a cyclic hydrazine compound S-8 by reaction with S-9. The resultant S-10 is then treated with phosgene to give the carbonyl chloride derivative S-11, which can further react with the hydroxyl-coupler compound to give the desired COUP—LINK—PUG compound S-12.

The following synthesis examples further illustrate preparation of a compound (A) as described:

SYNTHETIC EXAMPLE 1
PREPARATION OF COMPOUND 1

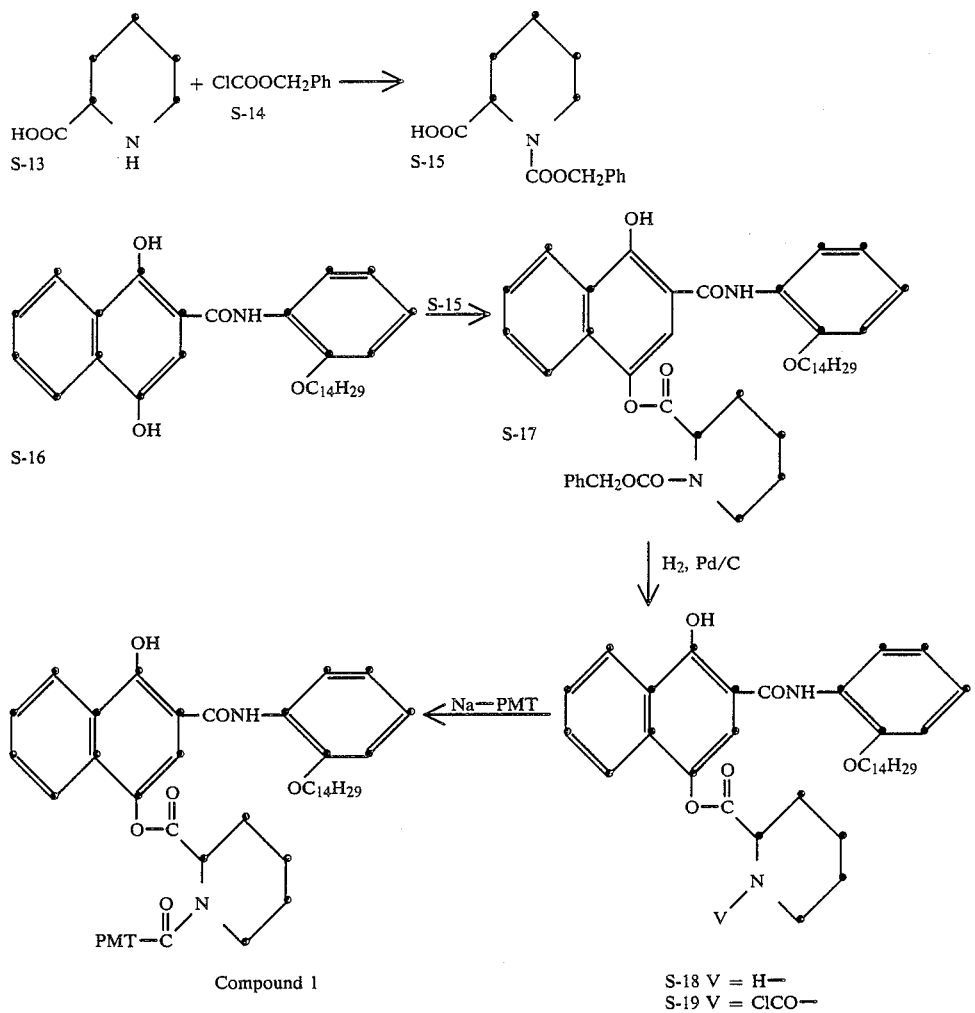

PREPARATION OF INTERMEDIATE S-17

To an ice/acetone cooled solution of 2-carboxypiperidine (S-13, 20 g, 155 mmol) in 2N NaOH (110 mL) was added dropwise over 1 hour and simultaneously benzyl chloroformate (S-14, 32 g, 186 mmol) and 2N NaOH solution (150 mL). After stirring 1 hour at room temperature, the crude product was dissolved in water and extracted with diethyl ether. The aqueous layer was acidified to pH 4 with HCl, then extracted with diethyl ether, the organic layers dried and concentrated giving S-15 as a clear oil. To a solution of coupler S-16 (40 g, 81.4 mmol), S-15 (23.6 g, 89.5 mmol), and dicyclohexylcarbodiimide in ethyl acetate (800 mL) was added N,N-dimethylaminopyridine catalyst (80 mg) and the resulting suspension was stirred overnight at room temperature. Filtration removed the dicyclohexylurea and one-half of the filtrate was concentrated and purified by silica gel chromatography to yield 15.5 g S-17 as a brown oil.

Conversion of S-17 to Compound 1

To a solution of S-17 (15.5 g, 21 mmol) in ethyl acetate (500 mL) was added 10% Pd on carbon catalyst and 60% HClO$_4$ (10 mL) and the mixture was hydrogenated at 45 psi 1 hour. The crystalline product was redissolved by addition of tetrahydrofuran and the catalyst removed by filtration through Celite. The filtrate was washed with water, dried over MgSO$_4$ (anhydr.), and concentrated to yield 12 g solid S-18. Next, 12% phosgene (34 mL, 41.5 mmol) and diethylaniline (1.32 mL, 8.3 mmol) were added to a solution of S-18 (5 g, 8.3 mmol) in dichloromethane (50 mL) and the mixture was stirred 1 hour at room temperature. Solvent was removed from the S-19 oil and replaced with pyridine (30 mL) and phenyltetrazolinethione sodium salt (Na—PMT, 1.7 g, 8.3 mmol) was added. After stirring 1.5 hours at room temperature the mixture was diluted with ethyl acetate and washed with 2N HCl solution. A fine precipitate was removed by filtration through Celite. The filtrate was dried, concentrated, and purified by silica gel chromatography to yield 1.5 g Compound 1, 99.6% pure, the structure of which was confirmed by mass spectral (m/e=806) and elemental analysis.

Calculated for C$_{45}$H$_{54}$N$_6$O$_6$S: %C=67.0, %H=6.7, %N=10.4, %S=54.0;

Found: %C=66.9, %H=6.9, %N=10.4, %S=53.7.

SYNTHETIC EXAMPLE 2
PREPARATION OF COMPOUNDS 3 AND 4

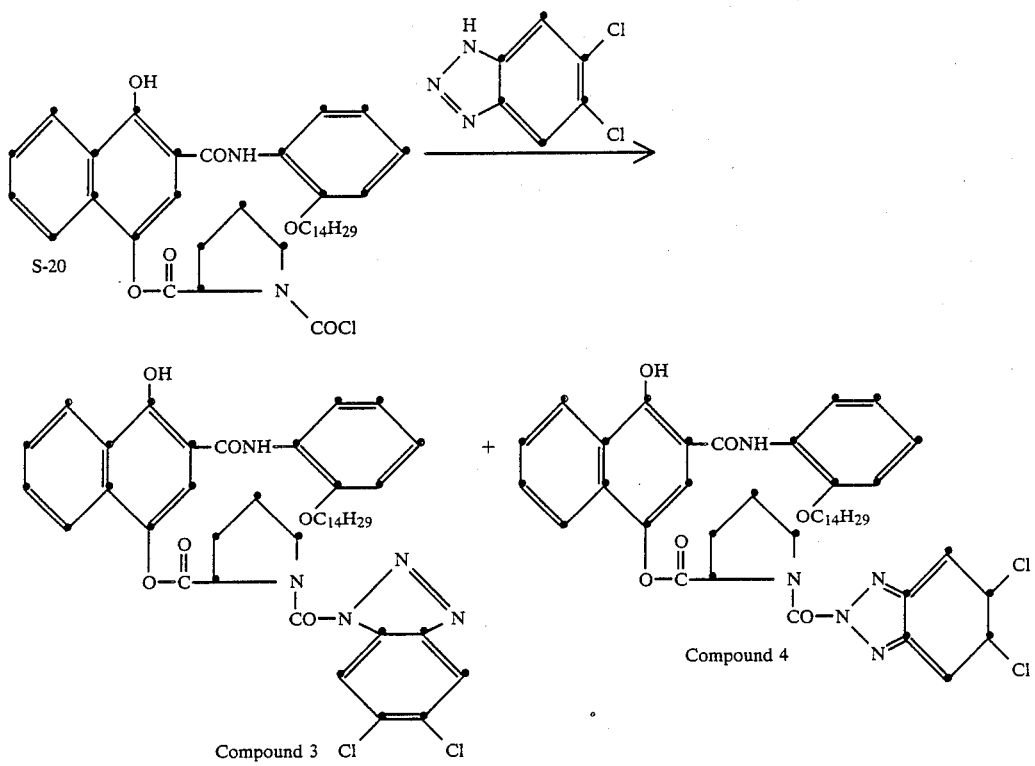

Preparation of Compounds 3 and 4

Intermediate S-20 was prepared in the same manner as S-19 described above except that the starting material L-proline was used in place of S-13. To a solution of S-20 (20.8 mmol) in pyridine (100 mL) was added 5,6-dichlorobenzotriazole (4.5 g, 23.9 mmol) followed by diisopropylethylamine (3.6 mL, 20.8 mmol). After stirring several hours, solvent was removed and replaced by ethyl acetate. This solution was washed with 2N HCl solution, brine, and then dried over MgSO$_4$ (anhydr.) and concentrated. Silica gel chromatography then yielded 8.0 g Compound 3 and 2.6 g Compound 4. Both showed the expected mass spectral peak at m/e=801 and the correct elemental analysis.

Calculated for $C_{43}H_{49}Cl_2N_5O_6$: %C=64.3, %H=6.2, %N=8.7, %Cl=8.8;

Found—Compound 3: %C=64.6, %H=6.3, %N=8.4, %Cl=8.6;

Found—Compound 4: %C=64.5, %H=6.0, %N=8.6, %Cl=9.3.

The following examples further illustrate the invention.

EXAMPLES 1-4

Photographic elements were prepared by coating the following layers on a cellulose ester film support (amounts of each component are indicated in mg/m$^2$):

| | |
|---|---|
| Emulsion Layer 1: | Gelatin - 2691; red-sensitized silver bromoiodide (as Ag) - 1615; yellow image coupler dispersed in dibutyl phthalate |
| Interlayer: | Gelatin - 624; didodecylhydroquinone - 113 |
| Emulsion Layer 2: | Gelatin - 2691; green-sensitized silver bromoiodide (as Ag) - 1615; cyan image coupler dispersed in dibutyl phthalate; DIR compound of Table I dispersed in N,N—diethyldodecanamide and coated at a level sufficient to provide a contrast to red light of 0.8 after a stepwise green light exposure and processing. |
| Protective Overcoat | Gelatin - 5382; bisvinylsulfonylmethyl ether at 2% total gelatin. |

Structures of the image couplers are as follows:

Cyan Image Coupler

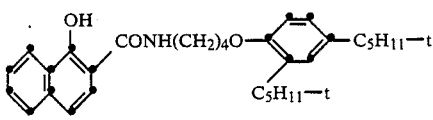

Yellow Image Coupler

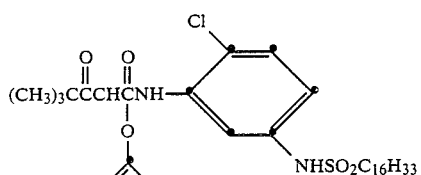

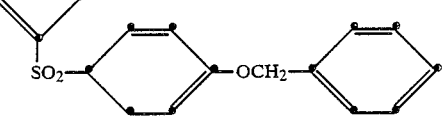

Strips of each element were exposed to green light through a graduated density steptablet, or through a 35% modulation fringe chart for sharpness measurements, and then developed 3.25 minutes at 38° C. in the following color developer, stopped, washed, bleached, fixed, washed and dried.

Color Developer

| | | |
|---|---|---|
| Distilled Water | 800 mL | |
| Sulfuric Acid | 2.0 mL | |
| Potassium Sulfite | 2.0 g | |
| CD-4* | 3.35 g | |
| Potassium Carbonate | 30.0 g | |
| Potassium Bromide | 1.25 g | |
| Potassium Iodide | 0.6 mg | |
| Distilled Water | to 1 L | |
| Adjust pH to 10.0 | | |

*4-amino-3-methyl-N—ethyl-N—β-hydroxyethylaniline sulfate.

Processed images were read with red light to determine the contrast and AMT acutance. From plots of AMT acutance vs. the logarithm of the contrast for variations in the coated level of each DIR compound, the acutance was determined at a contrast of 0.8. The acutance value for comparison compound C-1 was subtracted from each AMT value to provide the relative sharpness value reported as AMT in Table I. AMT calculations employed the following formula in which the cascaded area under the system modulation transfer curve is shown in equation (21.104) on p. 629 of the "Theory of the Photographic Process", 4th Edition, 1977, edited by T. H. James:

$$AMT = 100 + 66 \log[\text{cascaded area}/2.6696M]$$

where the magnification factor M=3.8 for the 35mm system AMT. The use of CMT acutance is described by R. G. Gendron in "An Improved Objective Method for Rating Picture Sharpness: CMT Acutance" in the Journal of the SMPTE, Vol. 82, pp. 1009-12 (1973). AMT is a further modification of CMT useful for evaluating systems which include the viewing of a positive print made from a negative. The couplers in these examples are as follows:

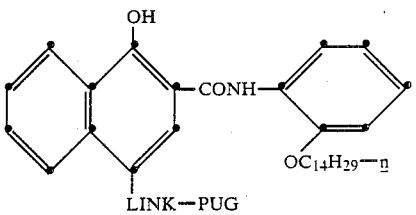

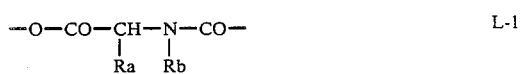
L-1

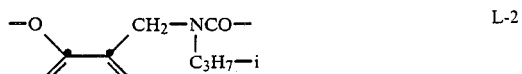
L-2

L-3

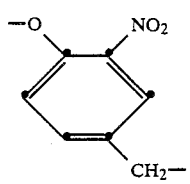

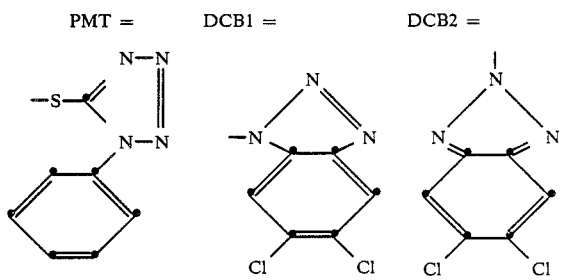

PMT =    DCB1 =    DCB2 =

TABLE I

| Examples | Compd. | Link | Ra | Rb | PUG | AMT |
|---|---|---|---|---|---|---|
| 1 Comparison | C-1 | L-2 | | | PMT | 0 |
| 2 Comparison | C-2 | L-3 | | | PMT | 2.0 |
| 3 Comparison | C-3 | L-1 | —H | —Ph | PMT | 2.4 |
| 4 Invention | 1 | L-1 | —(CH$_2$)$_4$— | | PMT | 3.5 |

The data in Table I show that a photographic element containing DIR compounds having a LINK group with a heterocyclic ring, as described, can provide greater sharpness than those containing closely related DIR compounds containing no such heterocyclic ring.

EXAMPLES 5-9

The half-life for release of the development inhibitor PUG from each DIR compound was determined in solution as a means for predicting the relative release rates when incorporated in film coatings. All reactions were carried out at a measured pH of 10.0+/−0.2 in aqueous 3% Triton X-100 (Triton X-100 is a trademark), ionic strength 0.375. Concentrations were chosen so that dye formation from COUP and LINK—PUG liberation would be complete in a fraction of a second. The rate of the coupling reaction and the limitations of hand pipetting imposed a one second lower limit on the range of half-lives which could be determined by this method.

To a scintillation vial with magnetic stirbar were added coupler stock (1.0 mL of 2 mMolar solution in aqueous 12% Triton X-100), pH 10 phosphate buffer (1.0 mL, ionic strength 1.5), and aqueous CD-2 developer compound (1.0 mL of 2 mMolar solution). At time zero, aqueous ferricyanide (1.0 mL of 4 mMolar solution) was added to the rapidly stirred mixture, allowed to react for variable time periods, and then quenched with aqueous HCl (1.0 mL of 1.0 mMolar solution). The amount of released development inhibitor was determined by high pressure liquid chromatography and a first order rate constant k for inhibitor release was calculated from the inhibitor concentration vs. reaction time data. The half-life of release reported in Table II was then calculated using the formula $t_{\frac{1}{2}} = \ln(2)/k$.

TABLE II

| Examples | Compd. | Link | Ra | Rb | PUG | $t_{\frac{1}{2}}$ Release (Sec.) |
|---|---|---|---|---|---|---|
| 5 Comparison | C-4 | L-1 | —H | CH₃ | PMT | 700 |
| 6 Invention | 2 | L-1 | —(CH₂)₃— | | PMT | 320 |
| 7 Comparison | C-5 | L-1 | —H | CH₃ | DCB1 | 53 |
| 8 Invention | 3 | L-1 | —(CH₂)₃— | | DCB1 | 530 |
| 9 Invention | 4 | L-1 | —(CH₂)₃— | | DCB2 | 4 |

Table II points out that structural modifications may be made in DIR compounds of the invention to control the rate of PUG release to be greater or smaller than that for closely related DIR structures.

The release of a useful compound from a carrier compound (A) can also be useful in other applications wherein controlled release is desired. Initiation of such release may be triggered by hydrolysis or redox reactions, for example. For example, the described —LINK—PUG group can release, for example, pharmaceutically useful moieties, including drugs, dyes, analytical agents, agricultural chemicals, and other useful moieties.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and at least one compound (A) having in a coupling position a coupling-off group capable of releasing a photographically useful group by means of intramolecular nucleophilic displacement wherein the compound (A) contains in the coupling position a releasable group represented by the formula:

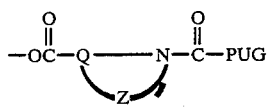

wherein
Q is N or C—R₁, where R₁ is hydrogen, unsubstituted or substituted alkyl, or unsubstituted or substituted aryl;
PUG is a photographically useful group; and
Z represents the atoms necessary to complete a non-aromatic, heterocyclic ring.

2. A photographic element as in claim 1 wherein the releaseable group is:

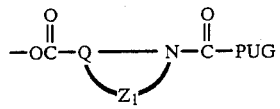

wherein Q is N or C—R₁, where R₁ is hydrogen, alkyl or aryl; Z₁ is (CH₂)ₘ where m is 3 or 4; and PUG is a photographically useful group.

3. A photographic element as in claim 1 wherein the compound (A) is a dye-forming coupler.

4. A photographic element comprising a support bearing at least one silver halide emulsion layer and a photographic coupler represented by the formula:

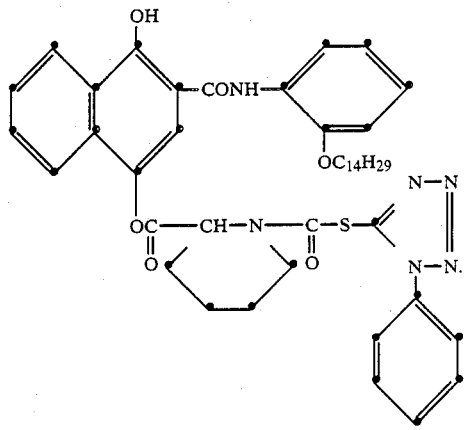

5. A photographic element comprising a support bearing at least one silver halide emulsion layer and a photographic coupler represented by the formula:

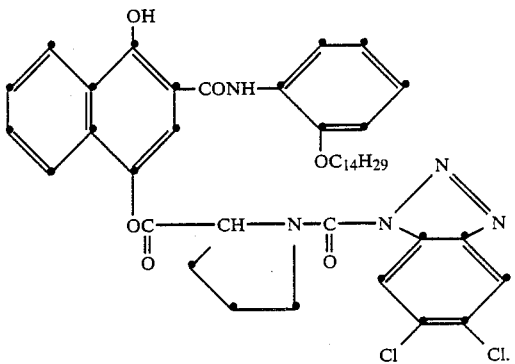

6. A photographic element as in claim 1 wherein PUG is a development inhibitor, dye, dye precursor, coupler, developing agent, ultraviolet radiation absorber, bleach inhibitor, bleach accelerator, development accelerator, silver complexing agent, fogging agent, or antifoggant.

7. A photographic element as in claim 1 comprising a support bearing at least one red-sensitive silver halide emulsion layer having associated therewith a cyan dye image providing material, at least one green-sensitive silver halide emulsion layer having associated therewith a magenta dye image providing material, and at least one blue-sensitive silver halide emulsion layer having associated therewith a yellow dye image providing material.

8. A process of forming a photographic image which comprises developing an exposed photographic silver halide emulsion with a color developing agent in the presence of a photographic coupler (A) capable of releasing a photographically useful group by means of intramolecular nucleophilic displacement wherein the coupler contains in the coupling position a releasable group represented by the formula:

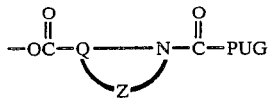

wherein

Q is N or C—$R_1$, where $R_1$ is hydrogen, unsubstituted or substituted alkyl, or unsubstituted or substituted aryl;

PUG is a photographically useful group; and

Z represents a bond or the atoms necessary to complete a non-aromatic ring.

9. A process as in claim 8 wherein the releasable group is:

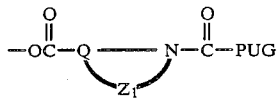

wherein Q is N or C—$R_1$, where $R_1$ is hydrogen, alkyl or aryl; $Z_1$ is $(CH_2)_m$ is 3 or 4; and PUG is a photographically useful group.

* * * * *